(12) United States Patent
Kumaraswamy et al.

(10) Patent No.: US 11,083,820 B2
(45) Date of Patent: Aug. 10, 2021

(54) ELASTIC MACRO POROUS SCAFFOLD AND A PROCESS FOR THE PREPARATION THEREOF

(71) Applicant: Council of Scientific & Industrial Research, New Delhi (IN)

(72) Inventors: Guruswamy Kumaraswamy, Pune (IN); Raja Rajamanickam, Pune (IN); Sayam Sengupta, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/762,196

(22) PCT Filed: Jan. 21, 2014

(86) PCT No.: PCT/IN2014/000040
§ 371 (c)(1),
(2) Date: Jul. 20, 2015

(87) PCT Pub. No.: WO2014/111960
PCT Pub. Date: Jul. 24, 2014

(65) Prior Publication Data
US 2015/0367035 A1 Dec. 24, 2015

(30) Foreign Application Priority Data

Jan. 21, 2013 (IN) .......................... 3959/DEL/2012
Jan. 24, 2013 (IN) ............................. 196/DEL/2013

(51) Int. Cl.
| | | |
|---|---|---|
| *A61L 27/44* | (2006.01) | |
| *A61L 27/56* | (2006.01) | |
| *A61L 27/50* | (2006.01) | |
| *B01J 20/10* | (2006.01) | |
| *B01J 20/26* | (2006.01) | |
| *B01J 20/28* | (2006.01) | |
| *B01J 20/30* | (2006.01) | |
| *A61L 27/46* | (2006.01) | |
| *B01J 20/04* | (2006.01) | |

(52) U.S. Cl.
CPC ............ *A61L 27/446* (2013.01); *A61L 27/46* (2013.01); *A61L 27/50* (2013.01); *A61L 27/56* (2013.01); *B01J 20/048* (2013.01); *B01J 20/103* (2013.01); *B01J 20/262* (2013.01); *B01J 20/28085* (2013.01); *B01J 20/3078* (2013.01)

(58) Field of Classification Search
None
See application file for complete search history.

(56) References Cited

U.S. PATENT DOCUMENTS

2011/0244003 A1* 10/2011 Kumaraswamy ....... A61L 27/10
424/400
2012/0149111 A1* 6/2012 Wegst .................. C12N 5/0619
435/395

OTHER PUBLICATIONS

Merriam-Webster™ "Merriam-Webster's Collegiate Dictionary, 11th edition," 2003; Merriam-Websters Inc; entry for "dispersion," and "ice", pp. 361 and 614.*
Lewis, Richard J., Sr.; "Hawley's Condensed Chemical Dictionary, 14th Edition," 2002; John Wiley & Sons; entry for "dispersion," p. 471.*
Dinu et al.; "Freezing as a path to build macroporous structures: Superfast responsive polyacrylamide hydrogels," 2007; Elsevier; Polymer, vol. 48, pp. 195-204.*
Kathuria et al.; "Synthesis and characterization of elastic and macroporous chitosan-gelatin cryogels for tissue engineering," 2009, Elsevier; Acto Biomaterialia, vol. 5, pp. 406-408.*
Smay et al.; "Directed Colloid Assembly of 3D Periodic Structures," 2002, Wiley-VCH; Advanced Materials, vol. 14, No. 18, pp. 1279-1283.*
Kumaraswamy et al.; "Soft Colloidal Scaffolds Capable of Elastic Recorvery after Large Compressive Strain," 2014, American Chemical Society, vol. 26, pp. 5161-5168.*
Gutierrez et al.; "Ice-Templated Materials: Sophisticated Structures Exhibiting Enhanced Functionalities Obtained after Unidirectional Freezing and Ice-Seggregation-Induced Self-Assembly," (2008) American Chemical Society, Chemistry of Materials, vol. 20, No. 3, pp. 634-648.*
Okay, Oguz et al.; "Superfast responsive ionic hydrogels with controllable pore size," (2005) Elsevier; Polymer, vol. 46, pp. 8119-8127.*
Gutierrez et al.; "Ice-Templated Materials: Sophisticated Structures Exhibiting Enhanced Functionalities Obtained after Unidirectional Freezing and Ice-Segregation-Induced Self-Assembly," 2008; American Chemical Society, Chemistry of Materials, vol. 20, No. 3, pp. 634-648. (Year: 2008).*
Okay; "Superfast responsive ionic hydrogels with controllable pore size," 2005, Elsevier; Polymer, vol. 46, pp. 8119-8127. (Year : 2005).*
Dinu et al., "Freezing as a Path to Build Macroporous Structures: Superfast Responsive Polyacrylamide Hydrogels," *Polymer* (2006), 48(1):195-204, Elsevier Science Publishers B.V.

* cited by examiner

*Primary Examiner* — Tigabu Kassa
*Assistant Examiner* — Ivan A Greene
(74) *Attorney, Agent, or Firm* — Dinsmore & Shohl, LLP (57) ABSTRACT

The present invention discloses elastic macro porous scaffold and a process for the preparation thereof. The present invention also provides a process for the preparation of macroporous, elastic nano particulate scaffolds comprising of coated or grafted cross linkable nanoparticles, and a crosslinker prepared by crosslinking during ice templating, wherein the modulus increases linearly with temperature.

3 Claims, 7 Drawing Sheets

ELASTIC MACRO POROUS SCAFFOLD AND A PROCESS FOR THE PREPARATION THEREOF

CROSS-REFERENCE TO RELATED APPLICATIONS

This application is a 35 USC § 371 National Stage application of International Application No. PCT/IN2014/000040 filed Jan. 21, 2014, now pending; which claims the benefit under 35 USC § 119(a) to India Application Serial No. 196/DEL/2013 filed Jan. 24, 2013 and to India Application Serial No. 3959/DEL/2012 filed Jan. 21, 2013. The disclosure of each of the prior applications is considered part of and is incorporated by reference in the disclosure of this application.

TECHNICAL FIELD OF INVENTION

The present invention relates to elastic Macro porous scaffold comprising amine coated particles wherein amine is in the range of 5-40% and a cross linker in the range of 5-40% and said scaffold characterized in that scaffold regains its shape after large compressional strain exceeding 50%. Particularly, the present invention provides a process for the preparation of macro porous scaffold comprising amine or imine coated brittle or plastic particles and a cross linker. Particularly, the present invention relates to scaffold regains its shape after large compression strain exceeding 50%. More particularly, the present invention relates to macroporous, elastic particulate scaffolds comprising of coated or grafted cross linkable particles, and a crosslinker prepared by crosslinking during ice templating, wherein the modulus increases linearly with temperature. Further the scaffolds exhibit significant organic and water sorption capacity and selectivity.

BACKGROUND AND PRIOR ART

Porous material scaffold with various shapes and size and ranging from nanoporous to microporous scaffolds find applications in various areas such as in tissue engineering, as optical materials, as catalysts, in electromagnetic devices, in cell growth amongst many others.

Macroporous materials that are currently available are based on polymeric materials such as porous polymers, mats or polymer fibers or are based on inorganic sol-gel materials or are based on assembly of organic or inorganic nanoparticles. While the said polymeric materials are flexible and have elasticity, they do not however possess mechanical properties that can be varied several fold, and do not have easily tunable surface characteristics such as wettability. Moreover, a serious limitation of the macroporous scaffolds based on inorganic/sol gel nanocomposites is that they are brittle and do not show large variation in mechanical properties.

Tissue engineering which emerged in the early 1990s to address the limitations of tissue grafting and alloplastic tissue repair offers a promising new approach to in tissue/organ repair. Its practical realization is connected with the development of suitable scaffold modulus that needs to match that of the tissue mass, where the material provides increased level of spatial organization and functionalities.

Simultaneously, it is imperative to provide a process for the preparation of macroporous scaffolds that can potentially generate scaffolds with morphological and mechanical properties more selectively designed to meet the specificity of tissue or bone-repair needs.

In Chem Comm 2012, 48 5292-5294, the inventor has disclosed the synthesis of functional hybrid silica scaffolds with controllable porosity by dynamic templating employing a surfactant, $C_{12}E_9$. While the scaffold disclosed may possess the desired porosity, it suffers from two drawbacks. It does not possess the elasticity properties desirable for tissue and bone repair applications. Also, for such clinical applications, it may be desirable to avoid use of ingredients such as surfactants, which may potentially lead to biocompatibility issues.

An article titled "Organic-Inorganic Hybrids of Hydroxyapatite with Chitosan" by K. H. Im J. H. Park et. al in Engineering Materials Vols. 284-286 (2005) pp. 729-732 disclose organic/inorganic macroporous elastic hybrids fabricated by solid-liquid phase separation and a subsequent freeze-drying process. However, these materials showed yield behaviour at strains of about 40% and for yield stress less than 0.3 MPa.

Materials with ordered macropores, can be synthesized through various methods, but a majority of them are synthesized using a "sacrificial" template. First, a template with a desired structure is prepared, and then the skeletal material is formed around the template. This is followed by removing the template by physical and/or chemical treatment such as phase-separated polymers, as colloidal crystals or microemulsions with macropores. But such removal process generally requires severe conditions such as extremely high or low pH and/or high temperatures.

The present inventors observed that porous materials can be prepared from a wide variety of starting materials, such as polymers, inorganics and metals, however, the intrinsic properties of inorganic or glassy materials render porous materials made from them mechanically fragile which prevents their use in many industrial application. Therefore, there is a need to provide porous material which is mechanically robust, is elastic that can completely recover their shape after large compressive strains.

Further, the processes in the art for preparation of macroporous scaffold employ harsh conditions, are not industrially viable, hence the inventors felt a need to provide a process which is simple, cheap, environment friendly and that can produce macroporous monolith with desired properties.

In ice templating (Gutiérrez, M. C.; Ferrer, M. L.; del Monte, F. Chem. Mater. 2008, 20, 634), an aqueous dispersion of polymers or colloids is frozen such that the growing ice crystals exclude the dispersed phase, consolidating it into the walls of a cellular solid. Directional ice freezing has been employed (Zhang, H.; Hussain, I.; Brust, M.; Butler, M. F.; Rannard, S. P.; Cooper, A. I. Nat Mater 2005, 4, 787.) to create aligned polymer, nanoparticulate and hybrid porous materials.

Since the properties of macroporous scaffolds depend on both the nature of the constituent materials and, on the architecture characterizing the network, a route to predominantly inorganic porous materials that recover elastically from large mechanical deformations and that can be prepared from a variety of inorganic starting materials remains elusive.

WO0158561 which relates to the field of separation of molecules, in particular biomolecules, from media containing said molecules disclose the packing material comprising an inorganic sorbent for use in separation of molecules, said sorbent comprising a cross-linked polymer coating to prevent non-selective adsorption and further comprising a spacer molecule comprising a coupling site. The polymer coating is a hydrophilic polymer coating comprising polyethyleneimine or derivatives thereof, and natural or synthetic hydrophilic polymers. The inorganic sorbent includes silica, controlled pore glass or, preferably, a metal oxide, such as alumina, zirconia, thoria or titania, or hydroxyapatite. The base support or core particles have a diameter in the range of 5 ym-3 mm in diameter, have a pore diameter of between 5-400 nm.

An article titled "Novel sorbents based on silica coated with polyethylenimine and crosslinked with poly(carboxylic acid): Preparation and characterization" by M. Ghoul, M. Bacquet et. al in Journal of Applied Polymer Science, Volume 90, Issue 3, pages 799-805, 17 Oct. 2003 DOI: 10.1002/app.12571 relate to sorbents based on silica coated with polyethylenimine (SilPEI) and crosslinked with poly (carboxylic acid) useful for heavy metal decontamination of aqueous solutions.

Article titled "Water Absorption and Diffusion Characteristics of Nano hydroxyapatite (nHA) and Poly(hydroxybutyrate-co-hydroxyvalerate-) based Composite Tissue Engineering Scaffolds and Nonporous Thin Films" by Naznin Sultana et. al. published in Journal of Nano materials, Volume 2013, Article ID 479109, 8 pages, relates to water uptake characteristics of poly(hydroxybutyrate-co-hydroxyvalerate) (PHBV-) based composite tissue engineering (TE) scaffolds incorporating nanosized hydroxyapatite (nHA) fabricated using the emulsion freezing/freeze-drying technique. The average pore diameter of the scaffold is in the range of 250-290 μm.

There are also several examples of sol-gel derived inorganic macroporous materials known in the art, like $SiO_2$—CaO and $SiO_2$—CaO—$P_2O_5$. Sol-gel derived nano/macroporous scaffolds is described in Physics and Chemistry of Glasses—European Journal of Glass Science and Technology Part B, Volume 48, Number 2, April 2007, pp. 65-68(4) by C. Marques et al; whereas sol-gel approach for synthesis of $TiO_2$ nanocrystals grafted on macroporous silica is disclosed in Applied Catalysis B: Environmental 104:282-290 (2011) by Maurizio Crippa et al.

In view of above, the macroporous scaffolds mainly comprise the polymers, further the pore size of the particles are more than or equal to 1.0 mm. Hence there is need for an accessible, macroporous cross linked material with smaller size particles, which improves the sorption properties of the material and can be useful in biotechnological/biomedical applications.

Also there is need for preparation of nanoparticle/polymer composite based macroporous material having selective hydrophobicity and controllable hydrophilicity, which might be able to effectively separate oil from oil/water mixtures, such as, in oil spills.

Though the freezing process for the preparation of scaffold is known, but a facile, improved process that leads to scaffold material having high selectivity, elasticity and sorption capacity is not known in the art. Also the scaffolds prepared by known freezing techniques gave brittle materials leading to poor absorption.

OBJECT OF THE INVENTION

The main object of the present invention is to provide elastic macro porous scaffold and a process thereof.

Another object of the present invention is to provide elastic Macro porous scaffold comprising amine coated particles wherein amine is in the range of 5-40% and a cross linker in the range of 5-40% and said scaffold characterized in that scaffold regains its shape after large compressional strain exceeding 50%.

Another object of the present invention is to provide a process for the preparation of scaffold regains its shape after large compression strain exceeding 50%.

Another object of the present invention is to provide a macroporous, elastic particulate scaffolds with desired pore dimension by a cross linking process involving ice-templating.

Another objective of the present invention is to provide the scaffolds exhibit significant organic and water sorption capacity and selectivity.

SUMMARY OF THE INVENTION

Accordingly, the present invention provides elastic macro porous scaffold comprising amine coated particles wherein amine is in the range of 5-40% and a cross linker in the range of 5-40% and said scaffold characterized in that scaffold regains its shape after large compressional strain exceeding 50%.

In an embodiment of the present invention the particles are selected from inorganic particles or organic lattices.

In one embodiment of the present invention said inorganic particles are silica nanoparticles or hydroxyapatite and organic lattices are glassy polymers selected from polystyrene or polymethylmethacrylate.

In another embodiment of the present invention the amine used for coating is primary or secondary amine selected from triamine, polyethylene imine or poly-epsilon-lysine.

In another embodiment of the present invention the cross linker used is selected from gluteraldehyde, or polyethyleneglycoldiglycidyl ether.

Still in another embodiment of the present invention optionally comprising modifying the hydrophilic scaffold with groups R—X, wherein —X is selected from carboxylic acids, aldehydes, acid chlorides, and R is selected from the aliphatic linear or branched chains of containing 8 to 50 carbon atoms as welt as aromatic groups to render the scaffold hydrophobic.

Still in another embodiment of the present invention A process for the preparation of macro porous scaffold as claimed in claim 1, wherein the said process comprising the steps of:
  (a) dispersing amine coated particles in the size range of 10 nm to 2 microns with a cross linker followed by rapid mixing at temperature ranging between 2-35° C. for a period ranging between 6-10 seconds to obtain a dispersion;
  (b) freezing the dispersion as obtained in step (a) in the refrigerator at temperature ranging between −18° C. to −196° C. for a period ranging between 5-24 hrs followed by allowing the ice to melt to leave behind the hydrophilic scaffold.

Still in another embodiment of the present invention the shear modulus and elastic modulus of the obtained scaffold ranges from $10^3$ to $10^6$ Pa.

Still in another embodiment of the present invention the porosity of the obtained scaffold is from 30% to 95%, the pore size varies from 1 to 200 microns and solvent absorption capacity is in the range of 1 g/g to 10 g/g.

Still in another embodiment of the present invention obtained scaffold is biocompatible and useful in tissue engineering.

DESCRIPTION OF FIGURES

FIG. 1: (A) depicts SEM of dry scaffold; (B) Confocal image of scaffold in the wet (as prepared) stage. These correspond to scaffolds prepared using polyethylene imine coated silica Ludox LS, 15 nm particles, frozen in the laboratory refrigerator (viz. at around −10° C.).

FIG. 2: depict SEM images of scaffolds prepared by freezing (A) in the laboratory refrigerator (viz. at around −10° C.), and (B) by cooling in liquid nitrogen.

FIG. 3: (A) depict Photographs of the macroporous elastic scaffolds during and after squeezing. (B) depict start-up of shear showing that the rheometer torque increases, shows an overshoot and does not relax. (C) depict temperature dependence of the solid modulus.

Average pore size: 55 μm

For Video see: docs.google.com/file/d/0B-D_pJdxFtKjRVpLR1JBX3ViRVk/edit

For video see: docs.google.com/file/d/0B-D_pJdxFtKjelB2X1NMY3RITWc/edit

DETAILED DESCRIPTION OF THE INVENTION

The invention will now be described in detail in connection with certain preferred and optional embodiments, so that various aspects thereof may be more fully understood and appreciated.

For the purposes of this document the following terms are defined:

Large compressional strain means a sprain exceeding 50%.

Brittle or plastic material means the material will not be able to recover its original shape form compressional strain beyond 5%.

The present invention relates to macroporous particulate scaffolds where the scaffold modulus are elastic, have mechanical properties that can be varied several hundred fold and the modulus is linearly related to temperature, prepared by crosslinking during ice-templating.

In the present context, elasticity means no decay in stress when 4-5% shear strain is applied. The material of the present invention can be compressed such that the final size is less than ten-fold smaller than the original size, such that the original size is rapidly regained on rehydration. Further, the properties for example, hydrophobicity/hydrophilicity; mechanical properties etc. can be readily varied.

The present invention discloses macroporous, elastic scaffolds comprising coated or grafted cross linkable particles in the size range of 10 nm to 2 microns, and a crosslinker, prepared by crosslinking during ice templating, wherein the modulus of the nano particulate assemblies increases linearly with temperature.

Macro porous scaffold comprising brittle or plastic particles in the range of 10 nm-2 microns and a cross linker, said particle being coated or surface grafted such that the scaffold regains its shape after large compressional strain exceeding 50%, said scaffold prepared by a process comprising:

(i) dispersing coated or grafted surface cross linkable particles and cross linking with a cross linker followed by freezing the dispersion; and (ii) allowing the ice to melt to leave behind the hydrophilic scaffold.

In the present invention, the macroporous elastic scaffolds are hydrophilic. The hydrophilic scaffold is modified with groups to render the scaffold hydrophobic. The groups are selected from materials of the form R—X, where —X is a group that can react with amine groups and R is a hydrophobic moiety. Therefore, X includes carboxylic acids, aldehydes, acid chlorides, etc. while R includes aliphatic linear or branched chains of containing 8 to 50 carbon atoms as well as aromatic groups.

The coated or grafted cross linkable particles are selected from inorganic particles such as silica nanoparticles (Ludox LS—15 nm; Ludox TM of the size of about 25 nm; Stober silica of the size of about 40 nm; colloidal silica of size 1-2 microns; hydroxyapatite of the size of about 200 nm, or polystyrene latex of size 300 nm to 2 microns.

The particles are coated with crosslinkable polymers, preferably a linear or branched polyamine containing primary, secondary, tertiary amine groups. In an optional embodiment, the scaffold is covalently surface modified using containing silane containing amine groups. The cross linker is selected from gluteraldehyde, or poly (ethylene glycol) diglycidyl ether diepoxide.

The process comprising the steps of;
i. The process for preparation of hydrophilic macroporous, elastic scaffold by the technique of crosslinking during ice templating comprises the following steps: dispersing coated or grafted surface cross linkable particles and cross linking with a crosslinker followed by freezing the dispersion; and
ii. allowing the ice to melt to leave behind the scaffold.

The process includes dispersing surface cross-linkable particles, either by coating of the particles (using electrostatic interactions to prepare coated particles) or surface grafting with an amine or an imine, followed by addition of a cross linker and freezing the dispersion. On freezing, the particles are segregated to the boundaries of the ice crystals. Crosslinking of the particles happens in the frozen state, for example, by formation of a Schiff base between glutaraldehyde and amine groups. After crosslinking, the ice is allowed to melt and the water is drained out, leaving behind the scaffold.

The present invention provides hydrophobic macroporous, elastic scaffold wherein the process further comprises vacuum drying the hydrophilic scaffold and dissolving in aqueous triethyl amine followed by addition of acid chloride selected from C8-C12 acid chloride in inert atmosphere and further washing with polar aprotic solvent. The polar aprotic solvent is selected from THF, DMF, acetonitrile, dichloromethane and such like. The macroporous, elastic scaffold prepared by the freeze drying method wherein the coated or grafted surface cross linkable particles is selected from the group consisting of:
  i. PEI-coated silica nanoparticles;
  ii. triamine grafted silica particles;
  iii. PEI coated hydroxyapatite particles;
  iv. PEI coated citrate capped hydroxyapatite particles; and
  i. PEI coated polystyrene.

In an aspect, the mechanical modulus of the scaffold varies from $10^3$ to almost $10^6$ Pa.

In another aspect, the scaffold is able to completely recover its original shape on compressive strain ranging up to 90%.

The porosity of the scaffold varies from 30% to 95% and the pore size varies from 5 microns to 200 microns.

The hydrophobic scaffold possess hydrocarbon absorption capacity in the range of 1 g/g to 10 g/g.

The macroporus scaffold find applications in tissue engineering, drug delivery, catalysis and such like sensors, electrically and thermally conducting elastic materials.

The highly selective elastic macroporous scaffold possesses adjustable solvo-philicity. The size of the particles in the macroporous nano-particulate assemblies according to invention is in the range of 10 nm-100 microns. The concentration of polymer is used in the range of 5 to 20% w/v with respect to the assembly or scaffold.

The hydrophilic macroporous scaffold prepared according to the invention can hold up to 10 to 20 times their weight in water. The water can be squeezed out of the material by gently compressing the scaffolds. The scaffolds have a shear modulus of between $10^3$ and $10^6$ Pa. On immersing in water, the scaffolds rapidly rehydrate. Additionally 100 micron to 10 cm long scaffolds rehydrates and regains their original dimensions in about 1-2 seconds. The porosity of the scaffold determines the amount of water that it can hold where the porosity can be readily varied by adjusting the nanoparticle content in the original aqueous dispersion.

According to the invention water sorption capacity of hydrophillic macroporous scaffold material was studied at different pH where the water uptake is a function of the pH of the water. It was found that the higher pH of water exhibited low water uptake capacity.

Figure 1A:
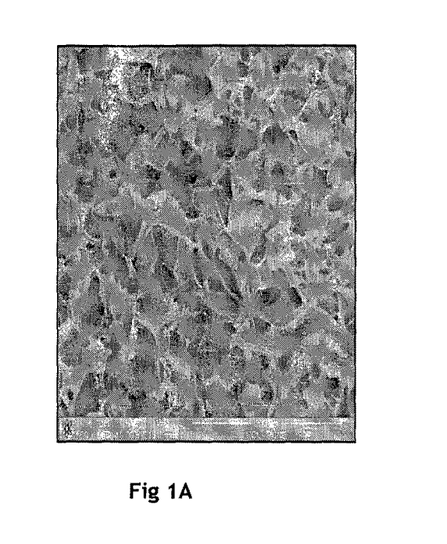
Figure 1B:
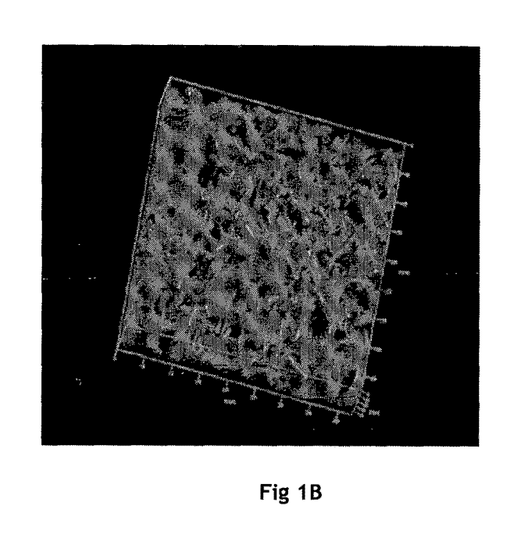

The data for prepared hydrophilic scaffolds, as a function of silica loading in the original dispersion, and for water at different pH, is shown in FIG. 1.

The process for the preparation of hydrophobic macroporous scaffold material comprises treating the so obtained hydrophilic scaffold with an alkyl acid chloride, in the presence of excessive amount of organic/inorganic base. The acid chloride reacted with residual primary amine groups from the polymer; preferably PEI, rendered the scaffold hydrophobic. Further the hydrophobic scaffold was soaked in water, and then immersed in organic solvent where its hydrocarbon sorption capacity was measured.

In the process the organic base used is selected from the group of aliphatic or aromatic amine such as diethylamide, triethylamine, pyridine, pyrrolidine, aniline, where the inorganic base is selected from the group of metal hydroxide such as NaOH, KOH, ammonia, metal carbonates, bicarbonates or hydrides; preferably the base is triethylamine; and alkyl acid chloride may be selected from the group (C1-C8) acyl chloride such as formyl chloride, acetyl chloride, benzoyl chloride.

Further the organic solvents are selected from the group consisting of toluene, ethyl acetate, benzene, lower alcohol such as methanol, ethanol, propanol, butanol, chloroform, tetrahydrofuran, acetone, acetonitrile or mixtures thereof.

The characteristics of hydrophobically modified elastic macroporous scaffolds, and comparison with performance of sawdust and other commercial materials called AbTech Smart Pak® are represented in Table 1 below:

TABLE 1

| Features | Sawdust | AbTech Smart Pak ® | Present Hydrophobic elastic macroporous material |
|---|---|---|---|
| Hydrocarbon sorption capacity (g/g) | 2-3 | 1-2 | 5 |
| Maximum water sorption capacity (g/g) | 5-6 | 0.06 | 0.02-0.04 |

TABLE 1-continued

| Features | Sawdust | AbTech Smart Pak ® | Present Hydrophobic elastic macroporous material |
|---|---|---|---|
| Hydrocarbon sorption capacity of water saturated sorbent (g/g) | — | 0.6-1.5 | 5 |
| Hydrocarbon to water selectivity | 0.4-0.6 | 18-25 | 125-400 |
| Rate of sorption | High | High | Rapid, few seconds for mm size sorbent samples |
| Hydrocarbon retention capacity | Poor | Good | Excellent, does not drip |

The elastic macroporous scaffold material obtained from the instant process exhibits adjustable solvo-phillicity, particularly high sorption capacity and rapid rate of sorption towards hydrocarbon and water.

The hydrocarbon to water selectivity of instant hydrophobic elastic macroporous material is in the range of 100-450. The hydrocarbon capacity of instant hydrophobic elastic macroporous scaffold material, where it selectively and rapidly sorb about 5-8 times its weight of hydrocarbon, whereas the hydrophilic material sorbs about 10-20 times its weight in water.

In the instant invention, the macroporous scaffold material was frozen with water. The material exhibits improved elastic properties with linear relationship between modulus and temperature where stiffness of material was increased with temperature.

The macroporous scaffold material exhibits improved elastic properties like rubber in hydrophillic condition.

The elasticity of the instant macroporous scaffold material can be compressed up to 10-15% with regards to its original solvated size, such that the original shape is recovered on re-solvation.

The present invention is explained by the following examples and experimental examples in more detail. The examples are intended to further illustrate the present invention and the scope of the invention cannot be limited thereby in any way.

EXAMPLES

Following are the examples given to further illustrate the invention and should not be construed to limit the scope of the present invention.

Materials and Method:

Polyethyl-enimine (25 kDa), polyethylenimine (2 kDa), poly (ethylene glycol) diglycidyl ether (Mn: 500) were used as received from Sigma Aldrich. 1 μm "Angstrom Sphere" silica particles were obtained from Richen Industry Limited, Hong Kong. Fluorescent PS latex particles (PS-Fluo-Red, Excitation: 530 nm, Emission: 518 nm) and monodisperse 300 nm silica particles were obtained from Microparticles GmbH, Germany, and were used as received. Glutaraldehyde, Calcium nitrate tetra hydrate (Ca (NO3)2.4H2O), Ludox TM particles (26 nm silica particles) were obtained as an aqueous dispersion from Sigma Aldrich and were used as received. Ammonium hydrogen phosphate ((NH4)2HPO4), 30% Ammonia solution in water were received from Merck and used without further purification. All the other chemicals and solvents were purchased from Merck India.

Experimental

Example 1

Preparation of Macroporous Nanoparticulate Scaffolds

To 1 ml of a 30% silica nanoparticle aqueous solution (corresponding to 300 mg of the particles) was added 160 μl of a 10% w/v PEI aqueous solution. This was made up to 3 ml by addition of distilled deionized water. To this, 150 μl of glutaraldehyde was added, and after rapid mixing (for less than 10 s), the dispersion was frozen in the refrigerator at −18° C. for 20 hrs. On freezing, the particles were segregated to the boundaries of the ice crystals. After crosslinking, the ice was allowed to melt and the water was drained out, leaving behind the desired scaffold.

Figure 2A:
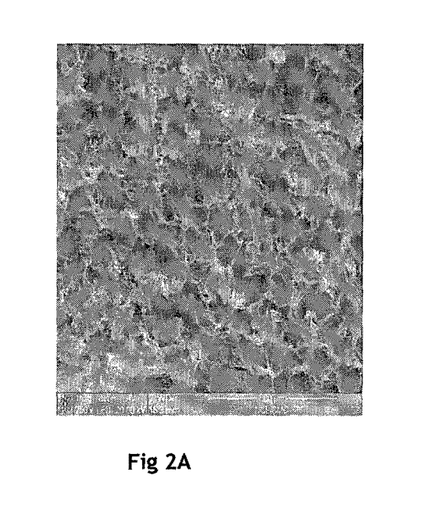
Figure 2B:
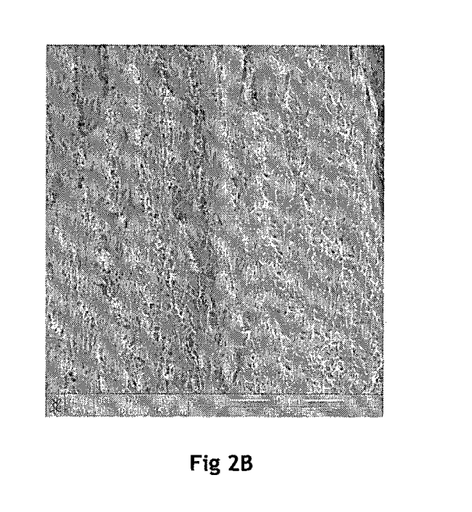

Characterization:

The structure of the scaffolds using SEM and confocal imaging revealed a porous scaffold, with strand-like or tape-like walls (FIG. 1). It was observed that the pore structure of the scaffold can be varied by changing the particle loading in the dispersion, or simply by changing the cooling rate at constant particle loading. For example, by changing the cooling rate by freezing in the laboratory refrigerator (around −10° C.) to rapid freezing in liquid nitrogen, the size of the template ice crystals were dramatically reduced such that the pore size could be varied from around 50 microns to about 1 micron (FIG. 2).

Properties:

Mechanical Properties:

Elasticity: While most nanoparticle-based scaffolds are brittle in nature, surprisingly, the scaffolds prepared using the present technique were highly elastic in nature. The elasticity was observed in the water-swollen state (as well as when swollen with polar solvents such as methanol, glycerine and DMSO).

Figure 3B:
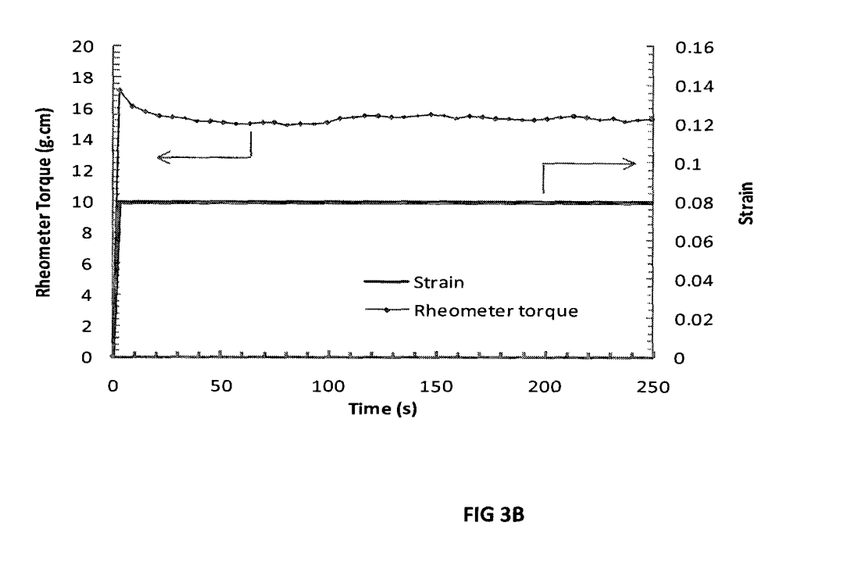
Figure 3C:
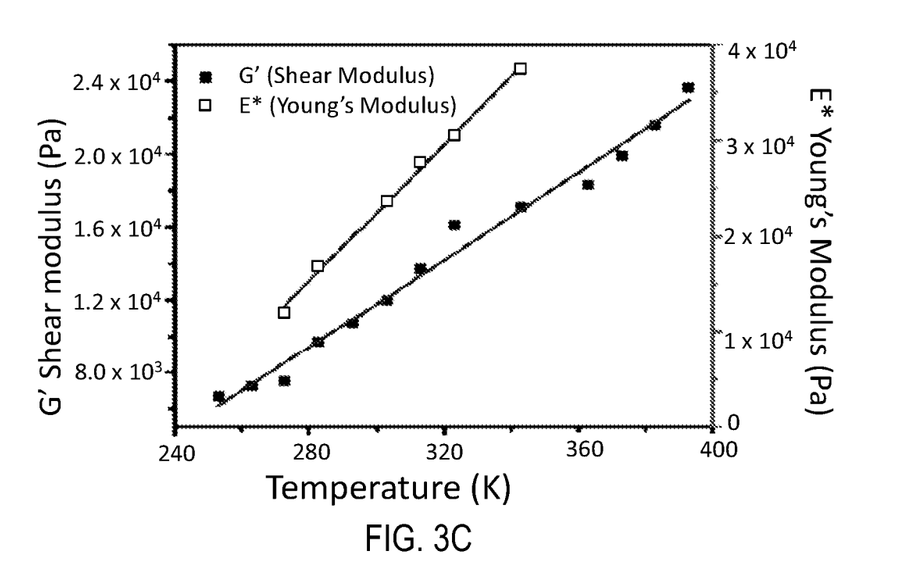
Figure 4:
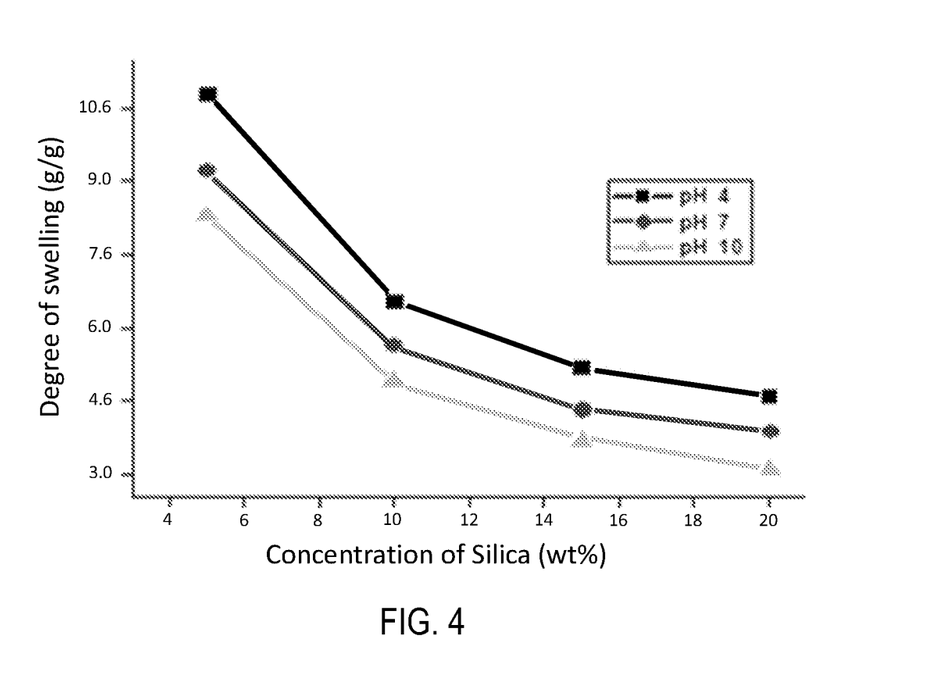
FIG. 4 depicts water sorption capacity of scaffolds. The degree of swelling is measured as weight of water taken up, normalized by the dry weight of the scaffolds.
Figure 5:
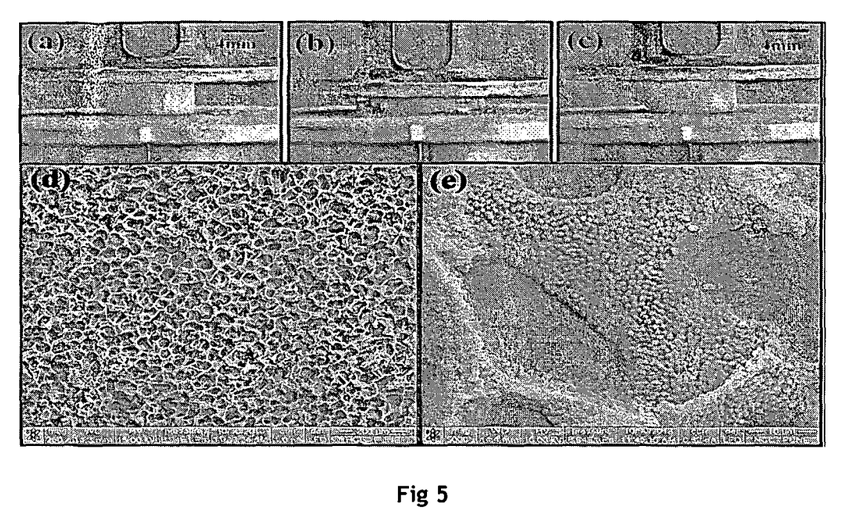
FIG. 5 Photographs that show the compression of scaffold prepared by ice templating a 20% w/v dispersion of 1 μm silica particles, with 25 kDa PEI and polyethylene-glycol-diglycidyl ether as the crosslinker (a) the initial state to (b) the compressed state (strain=50%) and (c) recovery on release of stress. (d) SEM image of scaffold prepared from a ϕ=20% w/v dispersion of 1 μm silica colloids. (e) Magnified section of the cross-linked scaffold.
Figure 6:
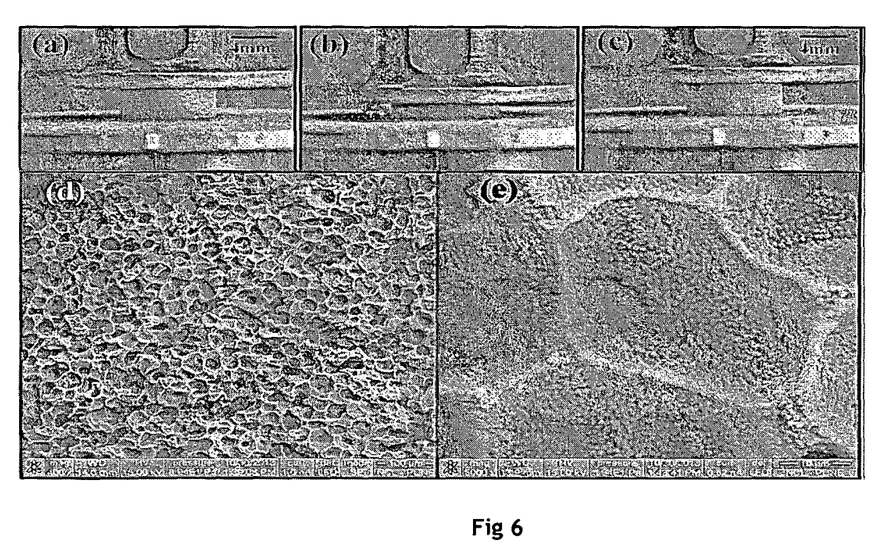
FIG. 6 Photographs that show the compression of scaffold prepared ice templating a 30% w/v dispersion of 1 μm silica particles, with 25 kDa PEI and polyethylene-glycoldiglycidyl ether as the crosslinker (a) the initial state to (b) the compressed state (strain=50%) and (c) recovery on release of stress. (d) SEM image of scaffold prepared from a ϕ=30% w/v dispersion of 1 μm silica colloids. (e) Magnified section of the cross-linked scaffold. Average pore size: 40 microns For video see: docs.google.com/file/d/0B-D_pJdxFtKjelB2X1NMY3RITWc/edit FIG. 7 Stress-compression ratio data from compression test on scaffolds prepared using 300 nm silica colloids ice templated from a ϕ=10% w/v dispersion. The various data indicate the different final compressive strains in each of the tests.
Figure 7:
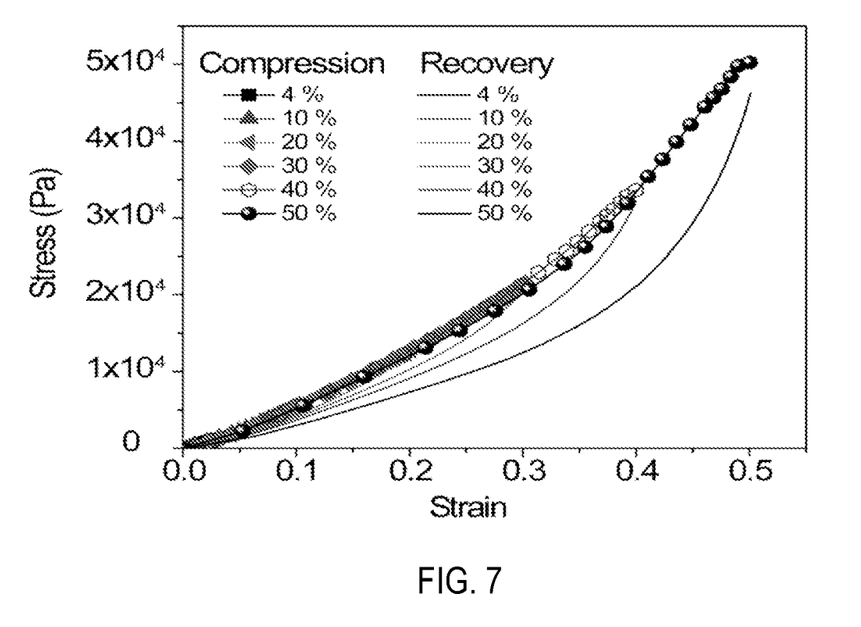
Figure 8:
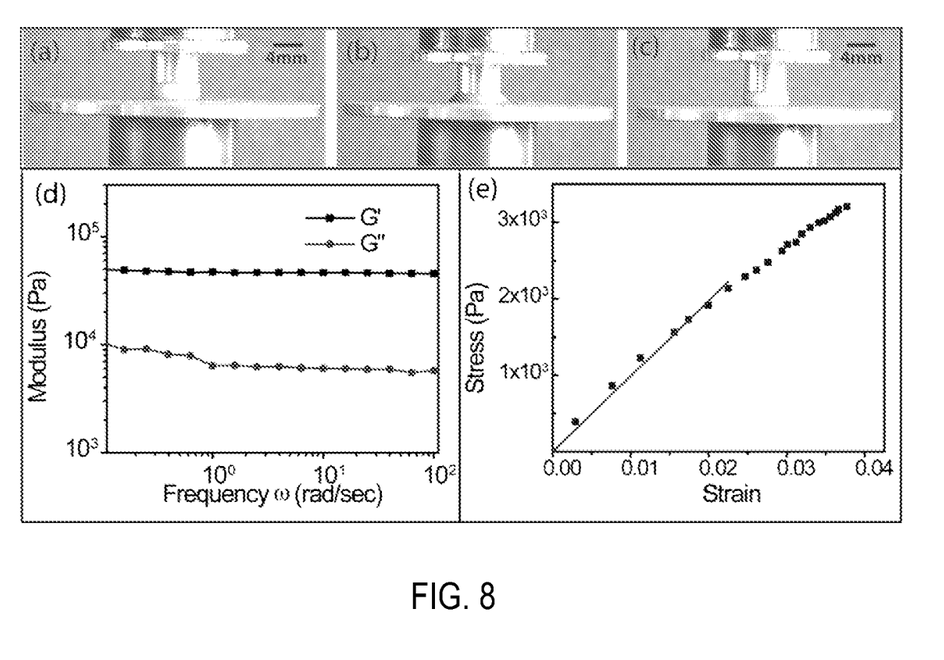
FIG. 8: Photographs that show the compression of scaffold prepared by ice templating a 10% w/v dispersion of 26 nm ludox silica nanoparticles, with 25 kDa PEI and polyethylene-glycoldiglcidyl-ether as the crosslinker. The photographs show (a) the initial state (b) the compressed state (strain=60%) and (c) recovery on release of stress. (d) Frequency sweep for these scaffolds. We observe that $G'=47087$ Pa at $\square=1$ rad/s. (e) Stress versus strain for compression test on the same scaffold. The elastic modulus, $E=98669$ Pa, is obtained as the slope of the initial linear region of the stress-strain data.
Figure 9:
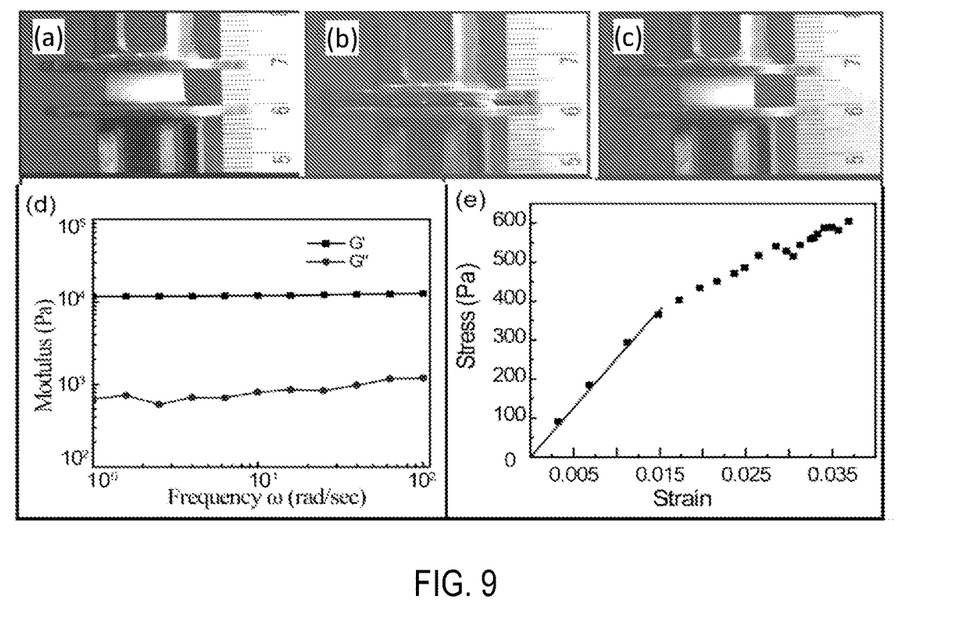
FIG. 9 Photographs that show the compression of scaffold prepared by ice templating a 10% w/v dispersion of 300 nm silica particles, with 25 kDa PEI and polyethylene-glycol-diglycidyl ether as the crosslinker. The photographs show (a) the initial state (b) the compressed state (strain=85%) and (c) recovery on release of stress. (d) Frequency sweep for these scaffolds. We observe that $G'=12090$ Pa at $\omega=1$ rad/s. (e) Stress versus strain for compression test on the same scaffold. The elastic modulus, $E=24574$ Pa, is obtained as the slope of the initial linear region of the stress-strain data.
Figure 10:
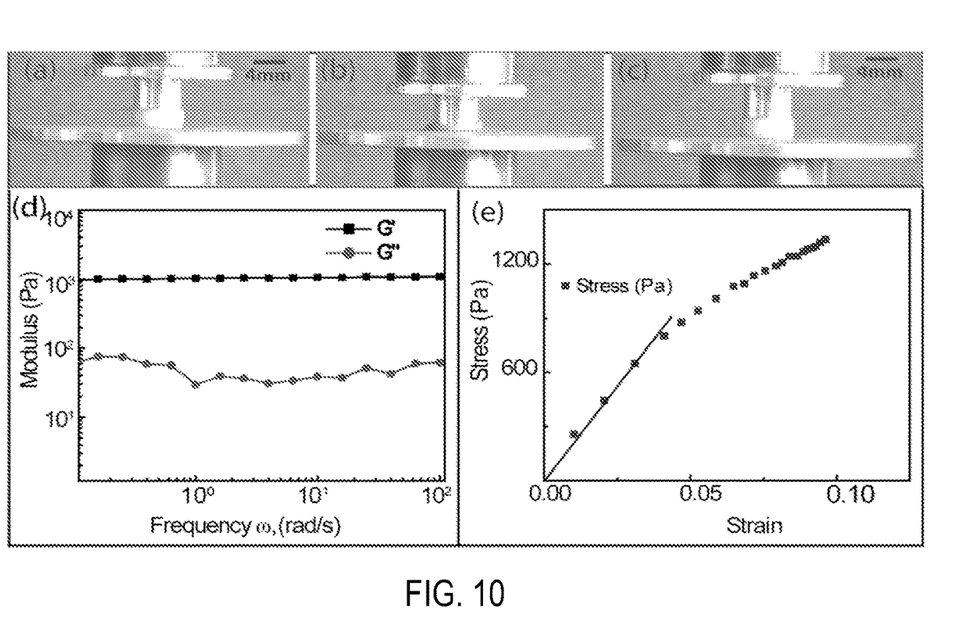
FIG. 10 Photographs that show the compression of scaffold prepared by ice templating a 10% w/v dispersion of 300 nm silica particles, with 2 kDa PEI and polyethylene-glycoldiglycidyl ether as the crosslinker. The photographs show (a) the initial state (b) the compressed state (strain=85%) and (c) recovery on release of stress. (d) Frequency sweep for these scaffolds. We observe that $G'=10323$ Pa at $\omega=1$ rad/s. (e) Stress versus strain for compression test on the same scaffold. The elastic modulus, $E=19710$ Pa, is obtained as the slope of the initial linear region of the stress-strain data.
Figure 11:
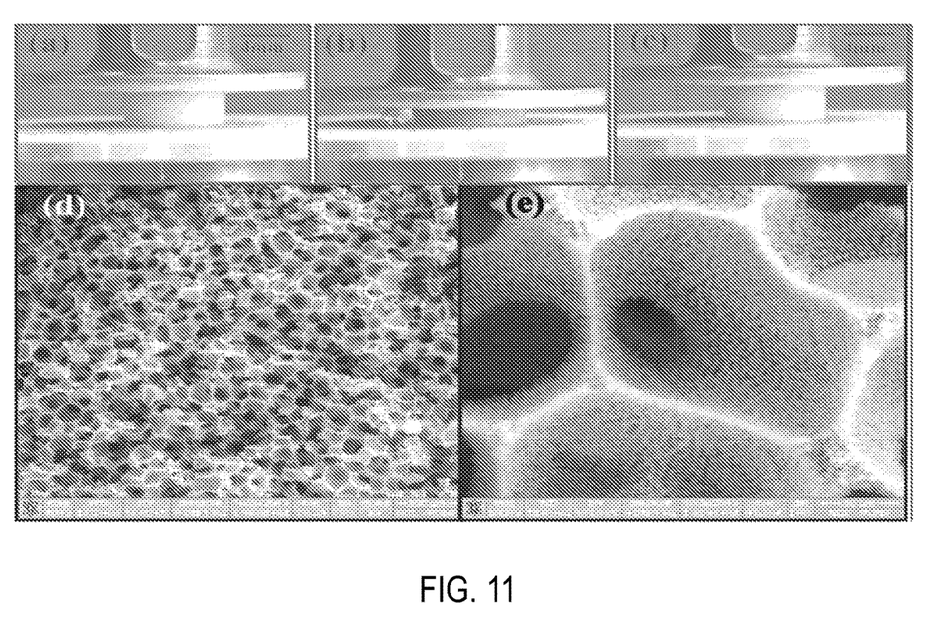
FIG. 11 Photographs that show the compression of scaffold prepared ice templating a 30% w/v dispersion of 1 μm silica particles, with 25 kDa PEI and polyethylene-glycol-diglycidyl ether as the crosslinker (a) the initial state to (b) the compressed state (strain=50%) and (c) recovery on release of stress. (d) SEM image of scaffold prepared from a ϕ=30% w/v dispersion of 1 μm silica colloids. (e) Magnified section of the cross-linked scaffold. Average pore size: 40 μm.
Figure 12:
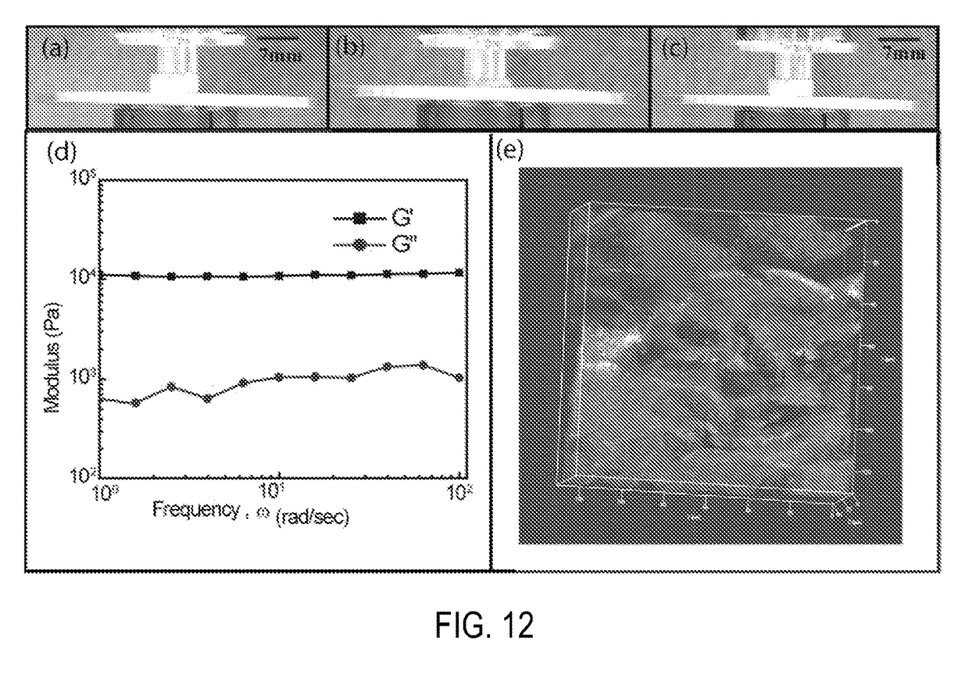
FIG. 12 Photographs that show the compression of scaffold prepared by ice templating a 10% w/v dispersion of 1 μm fluorescent polystyrene latex, with 25 kDa PEI and polyethyleneglycoldiglycidyl ether as the crosslinker. The photographs show (a) the initial state (b) the compressed state (strain=85%) and (c) recovery on release of stress. (d) Frequency sweep for 1 μm fluorescent polystyrene scaffold. We observe that $G'=11124$ Pa at $\square=1$ rad/s. (e) Confocal microscopy of scaffold prepared from 1 μm fluorescnt polystyrene latex colloids from a $\square=10\%$ w/v dispersion.

Large monolith scaffolds, up to several centimeters in size were prepared in the present invention. The mechanical properties of the elastic macroporous scaffolds were immediately evident. The scaffolds were soft, and could be compressed. On compression, the water was squeezed out of the scaffold (FIG. 3A). The scaffold recovered its original shape within seconds on immersing in water. The wet scaffolds were subjected to step shear in the rheometer (viz. strain was suddenly increased at t=0, and then held constant, FIG. 3B). On step shear, the stress in the sample increased, showing an overshoot, and then shows a constant value that does not decay with time. Even more interestingly, the wet scaffolds showed a linear increase in solid modulus with temperature (FIG. 3C). Most materials typically show a decrease in modulus with increase in temperature. The linear increase in modulus with temperature indicated the entropic origin of the elasticity in these materials. Such entropically elastic nanoparticulate assemblies are unprecedented. The shape recovery observed in FIG. 3A was also a manifestation of this entropic elasticity.

Further, the macroporous materials as prepared were highly hydrophilic and were able to hold up to about 10 times their weight in water, depending on the pH, ionic strength of the water and the structure of the scaffold.

The mechanical modulus of the scaffolds was observed to be frequency independent (over the measured range of 0.1 to 100 rad/s), as expected for an elastic solid. The mechanical moduli for scaffolds prepared from PEI-coated silica nanoparticles; triamine grafted silica particles and PEI coated hydroxyapatite particles can readily vary the modulus from about $10^3$ to almost $10^6$ Pa.

The elastic macroporous scaffolds prepared by the process of the present invention are described below in Table 1.

Example 2

Preparation of Hydrophilic Scaffolds

PEI Coated Silica Particles Stock Solution (0.5 mg/m$^2$ Coating Density):

To 300 mg of Ludox silica particle (600 mg from the 50% (W/W) Ludox TM Sigma Aldrich bottle, particle surface area: 140 m$^2$/g), was added 21 mg of 2 kDa PEI (210 µl of 10% w/v PEI solution in water, the pH which had adjusted to 4.5 using dilute HNO$_3$, Mw: 25000), the final weight was adjusted to 3000 mg using DI water and mixed vigorously using Spinix vibrating stirrer.

Scaffold Making:

To get a scaffold of 1 cm length and 0.8 cm diameter (it is the inner diameter of the glass vial being used to make the scaffold) sample: 600 µl of the above PEI coated Silica particle stock solution was taken in the glass vial of dimensions 5 cm length, 0.8 cm inner diameter and 0.1 cm thickness. To this 30 mg of Glutaraldehyde was added and mixed vigorously using Spinix vibrating stirrer.

The vial was frozen for 10 min in an ice bath of temperature −10° C. having ratio of 1:3 salt & ice cubes and kept inside the freezer of temperature −5° C. for 24 hrs. After one day the vial was thawed to get the scaffold out of the vial. Subsequently, sodium cyanoborohydride was added to the gel to reduce the imine groups formed upon cross-linking of PEI and glutaraldehyde. Finally the scaffold was washed with excessive water to remove unreacted glutaraldehyde and sodium cyanoborohydride to afford self standing scaffold.

Example 3

Preparation of PEI Coated Citrate Capped Hydroxyapatite Particles (Coating Density: 5 mg/m2)

Preparation of Citrate Capped Hydroxyapatite Particle 50 ml of 0.5 M Ca (NO3)2 and 0.3 M of (NH4)2HPO4 solutions were adjusted to pH 12 using 30% ammonia solution. Then, 50 ml of 0.3 M of (NH4)2HPO4 solution was taken in a double jacketed glass reaction chamber with overhead stirrer and the temperature was set at 60° C. Then, to the reaction mixture 50 ml of 0.5 M Ca (NO3)2.4H2O solution was added drop wise and white precipitate appears immediately after the addition of very first drop. The reaction mixture was stirred vigorously for 5 hrs. Then the white precipitate obtained was isolated by centrifugation, washed with abundant ethanol. Finally washed HAP in excess ethanol was evaporated using the Rotary evaporator and the dried sample was kept inside an inert atmosphere. The sample was calcined at 500° C. for 24 hrs. The HAP particles were characterized using DLS that yielded a mean size of 300 nm and by XRD that confirmed the formation of crystalline hydroxyapatite.

Preparation of PEI Coated Citrate Capped Hydroxyapatite Particles

To 100 mg of Citrate capped Hydroxyapatite particle (500 µL from the 20% (W/V) stock solution was added 10 mg of PEI (100 µl of 10% w/v PEI solution in water, the pH adjusted to 4.5 using dilute HNO3, Mw:25000), the weight was adjusted to 1000 mg using DI water and mixed vigorously using Spinix vibrating stirrer.

Scaffold Making:

To get a scaffold of 1 cm length and 0.8 cm Diameter (it is the inner diameter of the glass vial being used to make the scaffold) sample: 500 µl of the above PEI coated Cit-HAp particle stock solution is taken in the glass vial of dimensions 5 cm length, 0.8 cm inner diameter and 0.1 cm thickness. To this 30 mg of Glutaraldehyde was added and mixed vigorously using Spinix vibrating stirrer.

The vial was frozen for 10 min in an ice bath of temperature −10° C. having ratio of 1:3 salt & ice cubes and kept inside the freezer of temperature −5° C. for 24 hrs. After one day the vial was thawed to get the scaffold out of the vial. Subsequently, sodium cyanoborohydride was added to the gel to reduce the imine groups formed upon cross-linking of PEI and glutaraldehyde. Finally the scaffold was washed with excessive water to remove unreacted glutaraldehyde and sodium cyanoborohydride to afford self standing scaffold.

These scaffolds were characterized by compressing them in a TA ARES rheometer between roughened parallel plates. For compressional strains up to 85%, there was complete recovery of the sample dimensions on releasing the stress.

Example 4

Preparation of Hydrophobic Scaffolds

Completely dried Hydroxyapatite scaffold (crosslinked using Glutaraldehyde and reduced using Sodium cyanoborohydride) of length 0.5 cm & weight 0.2 g was taken in a 50 ml round bottom flask and degassed for 10 min. To this was added 1 ml of 1 M Triethylamine solution in water. The scaffold was allowed to swell for 5 min followed by adding dropwise 1 ml of 1 M Deconyl chloride with little stirring. The reaction mixture was kept for 4 hrs at room temperature to ensure efficient coupling. The scaffold was further washed 3-5 times with toluene.

The hydrocarbon sorption capacity was measured as follows: the modified scaffold of weight 0.2 g was dried completely. It was then immersed into large excess of DI water for water saturation and weighed. Then it was immersed into large excess of toluene and weighed. This procedure was repeated thrice with the same scaffold and average was taken.

The HC sorption capacity=Weight of toluene absorbed by water saturated scaffold/weight of water saturated scaffold (g/g).

Example 5

Methodology for Assembly of Nanoparticles for Making Scaffold Using Ice Templating Method Typically, 60 mg of 1 µm silica particles were dispersed in 520 µl of by sonication and vortexing for 15 min. To the aqueous dispersion of 1 µm silica particles, 3 mg (30 µl stock solution) PEI (25 KDa) was added and vortexed for 10 min. To this, 4 mg (40 µl stock solution) of polyethyleneglycoldiglycidyl ether was added and the sample was frozen at −18° C. for 24 hrs. The particle concentration in the overall composite was ~10 wt % water. After 24 hrs the scaffold was removed from refrigerator and allowed to reach the room temperature. Finally, the scaffold was washed with excessive water to remove unreacted polyethyleneglycoldiglycidyl ether.

(a) Preparation of 20% Silica Scaffolds.

To 120 mg of 1 um silica particles dispersed in 460 ul of water, 6 mg (60 ul stock solution) PEI (25 KDa) was added and vortexed for 10 min. To this, 8 mg (80 ul stock solution) of polyethyleneglycoldiglycidyl ether was added and the sample was frozen at −18° C. for 24 hrs. Then the scaffold was removed from refrigerator and allowed to reach the room temperature. Finally, the scaffold was washed with excessive water to remove unreacted polyethyleneglycoldiglycidyl ether.

(b) Preparation of 30% Silica Scaffolds.

To 120 mg of 1 um silica particles dispersed in 260 ul of water i.e), 6 mg (60 ul stock solution) PEI (25 KDa) was added and vortexed for 10 min. To this, 8 mg (80 ul stock solution) of polyethyleneglycoldiglycidyl ether was added and the sample was frozen at −18° C. for 24 hrs. Finally the scaffold was removed and washed with excessive water to remove unreacted polyethyleneglycol-diglycidyl ether.

(c) Polystyrene (PS) Scaffold:

To 10% (by weight) dispersion of 1 μm PS particles in aqueous medium was added 3 mg PEI (25 KDa) and vortexed for 10 minutes to coat the particles with PEI. To this, 4 mg (40 ul stock solution) of polyethyleneglycoldiglycidyl ether was added and the sample was frozen at −18° C. for 24 hrs. The scaffold was removed from refrigerator and allowed to reach the room temperature. Finally the scaffold was washed with excessive water to remove unreacted polyethyleneglycol-diglycidyl ether.

(d) Preparation of Scaffold from 300 nm Silica.

To 60 mg of 10% (by weight) aqueous dispersion of 300 nm silica particles was added 3 mg PEI (25 KDa) and vortexed for 15 min. To this 4 mg of polyethyleneglycoldiglycidyl ether was added and vortexed to homogenize the sample and immediately frozen at −18° C. for 24 hrs. After 24 hrs, the scaffold was removed from refrigerator and allowed to reach the room temperature. Finally the scaffold was washed with excessive water to remove unreacted polyethyleneglycoldiglycidyl ether.

2. The mechanical properties modulus (i.e hydrophobicity, hydrophilicity) and the scaffold microstructure (i.e pore size, pore dimensions etc.) can be easily varied by varying the ratio of cross linker.

3. The flexible modulus variation, which is of enormous importance, allows for use of the scaffold of the in tissue engineering applications where the prior art scaffold mechanical properties have to be adjusted to match those of the tissue of interest.

4. Advantageously, the flexibility of instant scaffold is tunable and pore dimension is controllable which allows the instant scaffold material useful for various industrial applications.

5. Further the scaffolds can undergo feasible chemical modification that improves the sorption capacity of organic and aqueous solvents.

We claim:

1. A process for the preparation of an elastic macro porous scaffold comprising the steps of:
   (a) dispersing particles in the size range of 10 nm to 2 microns, a cross linkable polymer with a cross linker followed by rapid mixing at a temperature ranging between 25 to 35° C. for a period ranging between 6-10 seconds to obtain a dispersion, wherein the particles are dispersed in an aqueous medium; and
   (b) freezing the dispersion obtained in step (a) in a refrigerator at a temperature ranging between −18° C. to −196° C. followed by cross linking in a frozen state for a period ranging between 5-24 hrs, followed by allowing an ice produced by freezing the dispersion to melt to leave behind a hydrophilic, elastic macroporous scaffold which regains its shape after large compressional strain exceeding 50%,
   wherein the particles are silica nanoparticles, the cross linkable polymer is linear or branched polyamine containing primary, secondary or tertiary amine groups, and the crosslinker is glutaraldehyde or polyethyleneglycoldiglycidyl ether,

TABLE 2

| Particle type | Particle amount (mg in 3 g total sample) | Amount of PEI coated (mg in 3 g total sample) | Glutaraldehyde conc. (mg) (in 3 g total sample) | Freezer temp. (° C.) | Storage Modulus G' (Pa) at 1 rad/s; 0.05% strain |
|---|---|---|---|---|---|
| Ludox LS Silica | 600 | 32.4 | 300 | −10 | 7.5E+05 |
| Ludox LS Silica | 450 | 24.3 | 225 | −10 | 1.89E+05 |
| Ludox LS Silica | 300 | 16.2 | 150 | −10 | 5.66E+04 |
| Ludox LS Silica | 150 | 8.1 | 75 | −10 | 4.84E+04 |
| Ludox LS Silica | 300 | 16.2 | 300 | −10 | 4.04E+05 |
| Ludox LS Silica | 300 | 16.2 | 150 | −10 | 5.66E+04 |
| Ludox LS Silica | 300 | 16.2 | 100 | −10 | 1.14E+04 |
| Ludox LS Silica | 300 | 16.2 | 50 | −10 | 3.81E+03 |
| Ludox LS Silica | 300 | 16.2 | 150 | −10 | 5.66E+04 |
| Ludox LS Silica | 300 | 16.2 | 150 | −45 | 1.10E+05 |
| Ludox LS Silica | 300 | 16.2 | 150 | −170 | 2.22E+05 |
| Ludox LS Silica | 300 | 14.2 | 150 | −10 | 8.39E+04 |
| Stober Silica 40 nm | 300 | 11.2 | 150 | −10 | 2.12E+04 |
| Triamine grafted silica | 300 |  | 150 | −10 | 6.96E+04 |
| Hydroxyapatite | 100 | 10 | 150 | −10 | 4.31E+04 |

Industrial Advantages:

1. The present invention provides the modulus of nano particulate assemblies by a technique of crosslinking of surface crosslinkable particles during ice templating that show entropic elasticity and recover completely after large compressive strains.

wherein the shear modulus and elastic modulus of the scaffold ranges from $10^3$ to $10^6$ Pa, wherein the porosity of the scaffold is from 30% to 95%, pore size varies from 1 to 200 microns and solvent absorption capacity is in the range of 1 g/g to 10 g/g, and wherein particle loading relative to particle, polymer and crosslinker is in the range of 64.4 wt. % to 89.55 wt. % in the initial dispersion.

2. The process of claim 1, wherein the scaffold is biocompatible and useful in tissue engineering.

3. The process of claim 1, wherein the linear or branched polyamine containing primary, secondary or tertiary amine groups of the cross linkable polymer is selected from polyethylene imine or poly-epsilon lysine.

* * * * *